(12) United States Patent
Kaesmann et al.

(10) Patent No.: US 12,295,903 B2
(45) Date of Patent: *May 13, 2025

(54) OVERHEAD EXOSKELETON

(71) Applicant: Hilti Aktiengesellschaft, Schaan (LI)

(72) Inventors: Simon Kaesmann, Munich (DE); Lars Melzer, Hohenfurch (DE)

(73) Assignee: Hilti Aktiengesellschaft, Schaan (LI)

( * ) Notice: Subject to any disclaimer, the term of this patent is extended or adjusted under 35 U.S.C. 154(b) by 706 days.

This patent is subject to a terminal disclaimer.

(21) Appl. No.: 17/414,845

(22) PCT Filed: Nov. 25, 2019

(86) PCT No.: PCT/EP2019/082383
§ 371 (c)(1),
(2) Date: Jun. 16, 2021

(87) PCT Pub. No.: WO2020/126321
PCT Pub. Date: Jun. 25, 2020

(65) Prior Publication Data
US 2022/0015980 A1 Jan. 20, 2022

(30) Foreign Application Priority Data

Dec. 17, 2018 (EP) ..................................... 18212922

(51) Int. Cl.
*A61H 3/00* (2006.01)
*A61H 1/02* (2006.01)

(52) U.S. Cl.
CPC ............ *A61H 3/00* (2013.01); *A61H 1/0281* (2013.01); *A61H 2003/007* (2013.01);
(Continued)

(58) Field of Classification Search
CPC ...... A61H 3/00; A61H 1/0274; A61H 1/0277; A61H 1/0281; A61H 2201/0165;
(Continued)

(56) References Cited

U.S. PATENT DOCUMENTS 1,257,297 A 2/1918 Brown
2,661,000 A * 12/1953 Gazeley ................ A61F 5/3753
602/16
(Continued)

FOREIGN PATENT DOCUMENTS

CN 107932478 A * 4/2018 ............. A01D 46/00
EP 3 189 945 A1 7/2017
(Continued)

OTHER PUBLICATIONS

Machine Translation of CN-107932478-A. Accessed from PE2E Search tool on Jan. 2024. (Year: 2018).*
(Continued)

*Primary Examiner* — Kendra D Carter
*Assistant Examiner* — Jaeick Jang
(74) *Attorney, Agent, or Firm* — Crowell & Moring LLP

(57) ABSTRACT

An exoskeleton for supporting an arm of a user includes a torso attachment device for releasably connecting the exoskeleton to a torso of the user, a bracket which is connectable to the torso attachment device, a lifting rod which is connectable to the torso attachment device via the bracket and which is reversibly movable in a first direction and a second direction relative to the bracket, a cantilever for supporting the arm of the user which is releasably connectable to the arm of the user, and a spring element. A force is exertable on the cantilever and the lifting rod by the spring element.

6 Claims, 9 Drawing Sheets

(52) U.S. Cl.
CPC ............... *A61H 2201/1253* (2013.01); *A61H 2201/1621* (2013.01); *A61H 2201/1638* (2013.01); *A61H 2201/1652* (2013.01); *A61H 2201/1671* (2013.01)

(58) Field of Classification Search
CPC .... A61H 2201/1215; A61H 2201/1246; A61H 2201/165; A61H 2201/1253; A61H 2201/1261; A61H 2201/1284; A61H 2201/1621; A61H 2201/1638; A61H 2201/1652; A61H 2201/1664; A61H 2201/1671; A61H 2201/1676; A61H 2205/0146; A61H 2205/0151; A61H 2205/0155; A61H 2205/0158; A61H 2205/0162; A61H 2205/0165; A61H 2205/06; A61H 2205/062; A61H 2205/084; A61F 5/01; A61F 5/0102; A61F 5/0118; A61F 5/013; A61F 5/3715; A61F 5/3723; A61F 5/3753
See application file for complete search history.

(56) References Cited

U.S. PATENT DOCUMENTS

| | | | | |
|---|---|---|---|---|
| 2,665,684 | A | * | 1/1954 | Llongueras ............ A61H 1/02 606/239 |
| 3,596,655 | A | * | 8/1971 | Corcoran ............ A61H 1/008 297/391 |
| 5,385,536 | A | * | 1/1995 | Burkhead ............ A61F 5/3753 602/5 |
| 9,205,017 | B2 | | 12/2015 | Doyle |
| 9,737,374 | B2 | | 8/2017 | Doyle |
| 10,058,994 | B2 | | 8/2018 | Angold et al. |
| 2011/0021962 | A1 | * | 1/2011 | Sorrenti ............ A63B 21/025 602/20 |
| 2015/0335455 | A1 | * | 11/2015 | Sorrenti ............ A61F 5/0123 602/16 |
| 2017/0173783 | A1 | | 6/2017 | Angold et al. |
| 2021/0275380 | A1 | * | 9/2021 | Finke ............ B25J 9/0006 |
| 2021/0386577 | A1 | * | 12/2021 | Bleau ............ A61F 5/3753 |

FOREIGN PATENT DOCUMENTS

| | | | |
|---|---|---|---|
| JP | 2011-251057 | A | 12/2011 |
| JP | 2014-172129 | A | 9/2014 |
| JP | 2017-159442 | A | 9/2017 |
| JP | 6416353 | B1 | 10/2018 |
| KR | 10-2018-0059034 | A | 6/2018 |
| KR | 10-1896181 | B1 | 9/2018 |
| WO | WO 2009/076725 | A1 | 6/2009 |
| WO | WO-2020094549 | A1 * | 5/2020 ........... A61F 5/0102 |

OTHER PUBLICATIONS

PCT/EP2019/082383, International Search Report dated Jan. 28, 2020 (Three (3) pages).

U.S. Patent Application, "Device for Supporting and Relieving the Arms of a User", filed Jun. 16, 2021, First Named Inventor: Simon Kaesmann.

U.S. Patent Application, "Device for Compensating a Shoulder Elevation in a Passive Exoskeleton", filed Jun. 16, 2021, First Named Inventor: Simon Kaesmann.

U.S. Patent Application, "Neck Switch Device in a Passive Exoskeleton", filed Jun. 16, 2021, First Named Inventor: Simon Kaesmann.

* cited by examiner

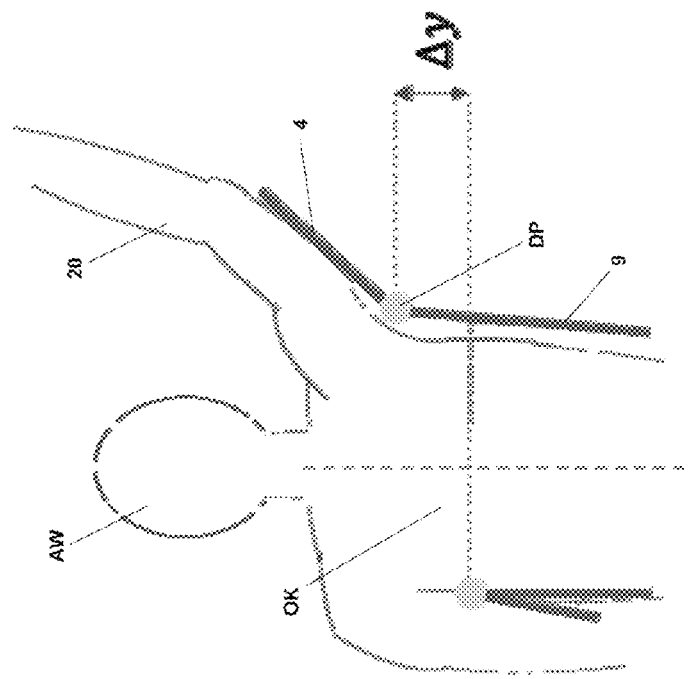
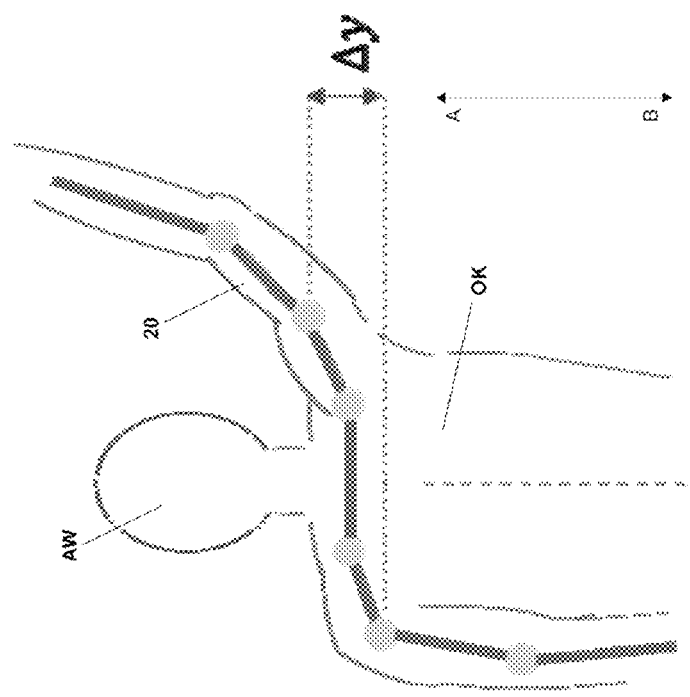

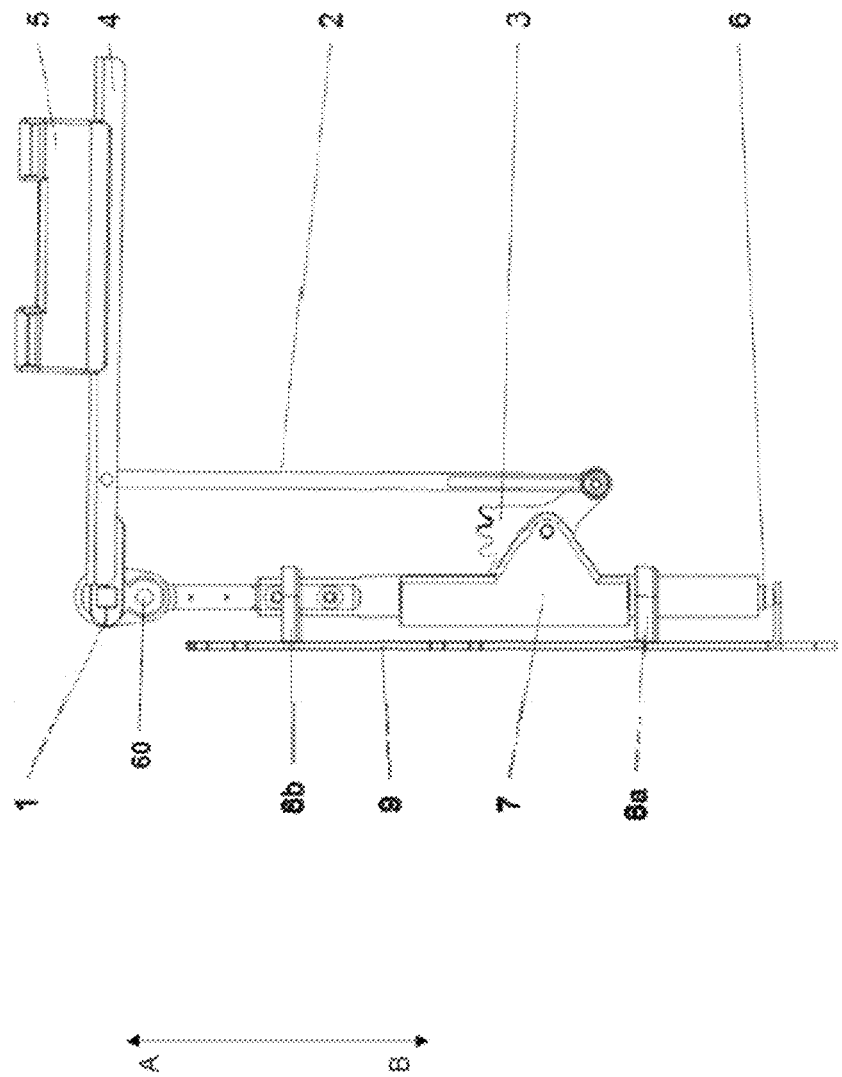

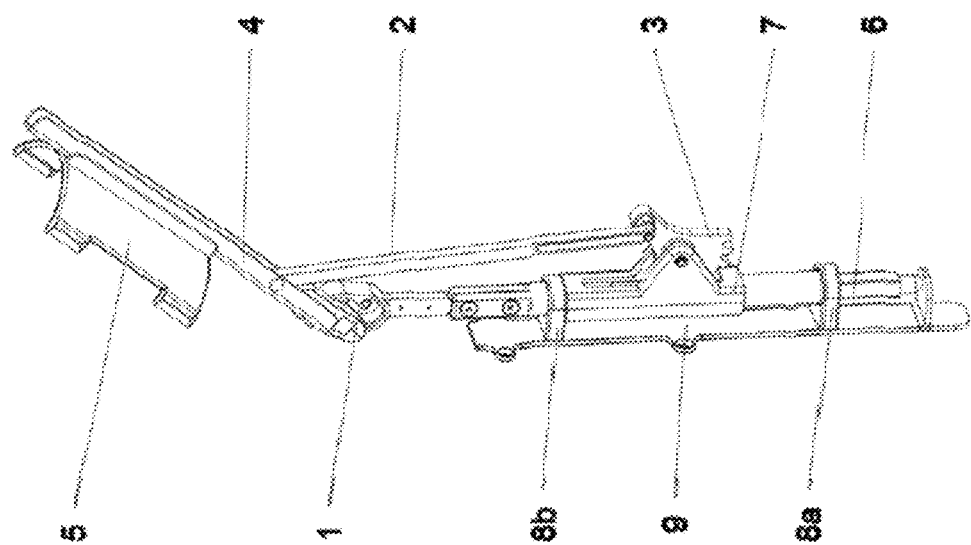
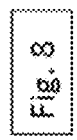

OVERHEAD EXOSKELETON

BACKGROUND AND SUMMARY OF THE INVENTION

The present invention relates to an exoskeleton for supporting at least one arm of a user.

Exoskeletons that are available on the market and are available for the passive and/or active support of the extremities of a user, in particular the arms, usually include a hip fastening, a first and second supporting strut, and a first and second arm support. The first and the second supporting strut are vertically fastened to the left-hand and right-hand side, respectively, of the hip fastening. At the upper end of the first supporting strut, the first arm support is fastened in a rotatable manner via a pivot bearing. Likewise, at the upper end of the second supporting strut, the second arm strut is fastened in a rotatable manner via a further pivot bearing. The arm supports can be fixed in different angular positions relative to the supporting strut, such that the arms of the user can be rested on the deployed arm supports. With the aid of springs, the arm supports can push the arms of the user upward and as a result make it easier to lift a significant load (i.e., one with a great weight).

As a result of the anatomy of the human shoulder, as is schematically shown in FIG. 1a, when the arms are lifted, the shoulder joint is elevated at the same time. In exoskeletons according to the prior art, the pivot bearings between an upper supporting strut and arm support remain in one position, however, and do not follow the elevation of the human shoulder joint. This can result in a troublesome relative movement between the exoskeleton and the arms. This has the result that either the arms are forced onto a path of motion that is not desired by the user or the attachment points between the exoskeleton and human body slip. Movement restrictions and low wearing comfort are the result. An exoskeleton of this kind according to the prior art is shown for example in the U.S. Pat. Nos. 9,205,017 BB and 9,737,374 BB.

The object of the present invention is to solve the above-mentioned problem and in particular to provide an improved exoskeleton for supporting at least one arm of a user.

This object is achieved by an exoskeleton for supporting at least one arm of a user.

According to the invention, the exoskeleton contains a torso attachment device for releasably connecting the exoskeleton to a torso of a user, at least one bracket, which is connectable to the torso attachment device, a lifting rod, which is connectable to the torso attachment device by means of the at least one bracket and which is reversibly movable in a first and a second direction relative to the bracket, a cantilever for supporting the arm of a user, which is releasably connectable to the arm of a user, and a spring element for exerting a force on the cantilever and the lifting rod. As a result, an exoskeleton is provided, which allows a resting possibility for the arms of a user which is adapted to the elevation of the human shoulder joint when the arm is lifted. As a result of this ergonomically or anatomically correct resting possibility for the arms of a user, better support can be achieved for the user when holding heavy loads.

According to an advantageous embodiment of the present invention, a coupling rod having a first and a second end can, the coupling rod being rotatably connected respectively to the cantilever by the first end and to the lifting rod by the second end via a compensating mechanism. By way of the coupling rod, the movement of the cantilever relative to the lifting rod is guided and supported. An undesired lateral movement of the cantilever or twisting or torsion of the cantilever with respect to the lifting rod and/or bracket can be prevented as a result.

According to an advantageous embodiment of the present invention, the compensating mechanism can be configured in the form of a slot at the second end of the coupling rod and of a pivot bearing on the lifting rod, wherein the pivot bearing is positioned in the slot. As a result, the compensating mechanism can be implemented in a simple manner. Furthermore, as a result of the slot at the end of the coupling rod, the cantilever can be lowered (i.e., moved downward) without exerting a force on further components.

According to an advantageous embodiment of the present invention, the compensating mechanism can be configured in the form of a slotted guide between the second end of the coupling rod and the lifting rod. This ensures reliable guidance of the second end of the coupling rod.

According to an advantageous embodiment of the present invention, the compensating mechanism can be configured in the form of a sector gear and of a rack, wherein the sector gear is rotatably connected to the lifting rod such that the teeth of the sector gear mesh with the teeth of the rack. The sector gear can also be referred to as a partial gear. As a result, effective guidance for avoiding an undesired lateral movement of the cantilever or twisting or torsion of the cantilever with respect to the lifting rod and/or bracket can be achieved in a simple manner. With the aid of the slot at the end of the coupling rod, the cantilever can be lowered (i.e., moved downward) without exerting a force on the sector gear.

According to an advantageous embodiment of the present invention, rather than the compensating mechanism, the articulated connection between the cantilever and the lifting rod can be embodied by a spindle or an actuator in order to move the cantilever upward. Rather than a mechanical coupling between the cantilever and the lifting rod, the angular position or the angle of the arm strut with respect to the lifting rod can also be determined via sensors, in order to correctly determine the elevation of the cantilever.

According to an advantageous embodiment of the present invention, the lifting rod and the rack can be configured as a piston-cylinder unit. As a result, the attachment of the lifting rod and the rack to the bracket can be implemented in a space-saving manner.

Further advantages will become apparent from the following description of the figures. The figures illustrate various exemplary embodiments of the present invention. The figures, the description and the claims contain numerous features in combination. A person skilled in the art will expediently also consider the features individually and combine them to produce useful further combinations.

In the figures, identical and similar components are denoted by the same reference signs.

BRIEF DESCRIPTION OF THE DRAWINGS

FIG. 1a shows a front view of a human torso with a number of schematically illustrated joint points;

FIG. 1b shows a further front view of a human torso with a number of schematically illustrated joint points;

FIG. 7 shows a side view of the cantilever, the bracket, the spring element and the lifting rod of the exoskeleton according to the invention in the second setting;

FIG. 8 shows a perspective view of the cantilever, the bracket, the spring element and the lifting rod of the exoskeleton according to the invention in a third setting.

DETAILED DESCRIPTION OF THE DRAWINGS

Figure 3:
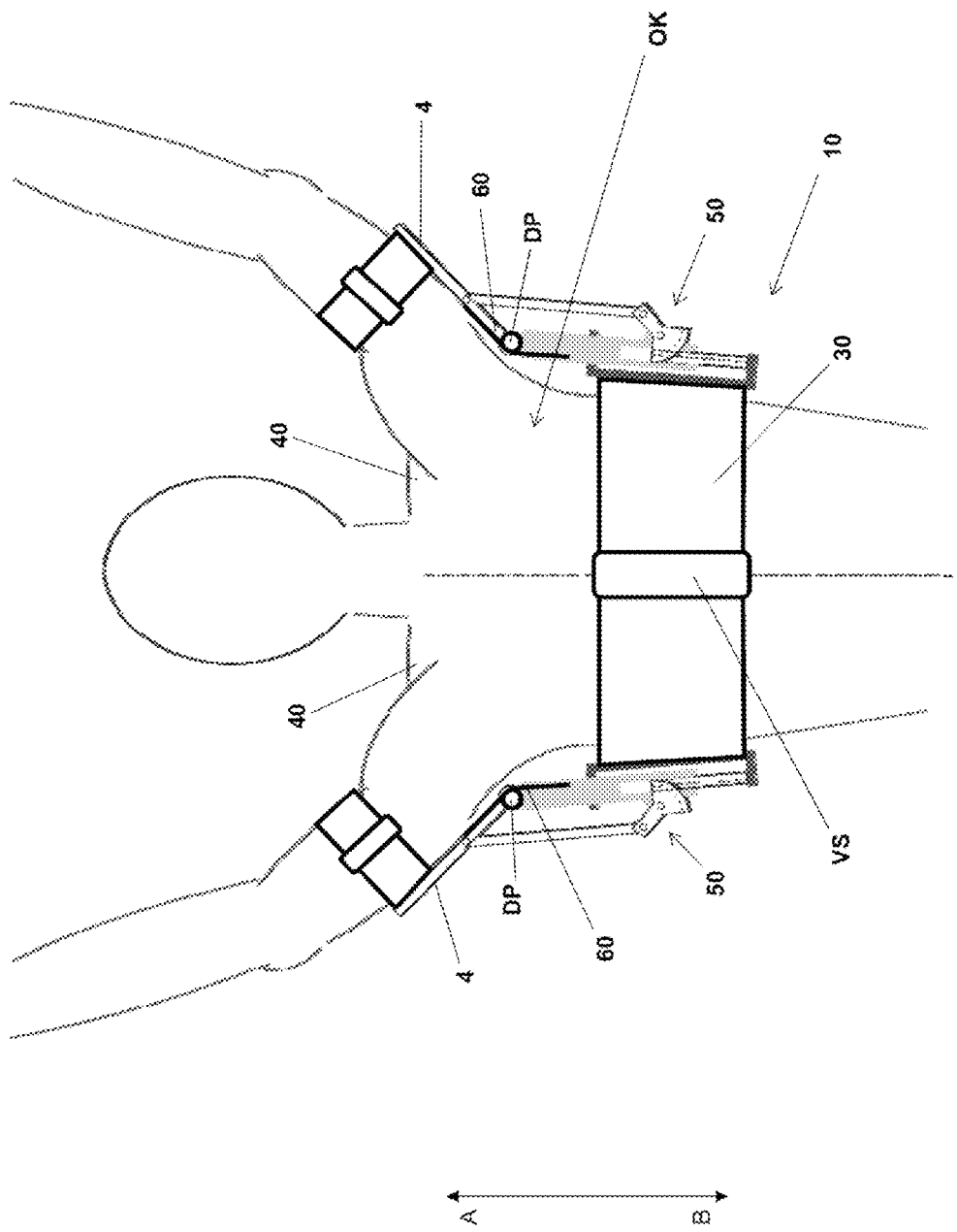
FIG. 3 shows a schematic illustration of the exoskeleton according to the invention for supporting two arms of the user.

FIG. 3 shows a front view of a human upper body OK of a user AW, on which an exoskeleton 10 for supporting or increasing the work performance of the arms 20 of a user AW is arranged.

The exoskeleton 10 contains substantially a torso attachment device 30, a bracket 9, a lifting rod 7, a cantilever 4, and a spring element 60.

As indicated in the figures, a joint element 1 can be provided between the cantilever 4 and the lifting rod 7, in order to connect the cantilever 4 and the lifting rod 7 together in a pivotable manner.

The torso attachment device 30 serves to releasably connect the exoskeleton 10 to a torso (i.e., the upper body OK) of a user AW (cf. FIG. 3). The torso attachment device 30 can in this case be configured in the form of a hard shell, of a flexible chest strap or belt. Furthermore, the torso attachment device 30 contains a closure VS, arranged in the middle of the chest of the user AW, with which the torso attachment device 30, configured for example as a chest strap, can be opened and closed. The closure VS can be configured for example as a touch-and-close fastener or as a belt buckle.

According to an alternative embodiment (not shown in the figures) of the exoskeleton 10 according to the invention, the torso attachment device 30 can also be configured in the form of a hip belt and consequently be positioned on the hips or pelvis of the user AW. In addition, one or two straps can be fastened for fixing the torso attachment device 30 at the shoulders 40 of the user AW or for preventing the torso attachment device 30 from slipping in the arrow direction B. These straps (not illustrated in the figures) can be guided from the front side of the torso attachment device 30 configured as a chest strap or belt, over the shoulders 40 of the user AW (i.e., in a similar manner to suspenders), to the rear side of the torso attachment device 30.

As shown in FIGS. 4 to 9, the bracket 9 is configured substantially as a flat metal sheet with four circular cutouts 11 and a first plain bearing 8a and a second plain bearing 8b. The four cutouts 11 can also be referred to as screw bosses and serve for laterally attaching the bracket 9 to the torso attachment device 30. For this purpose, four screws or rivets can be driven through the four cutouts 11 in the bracket 9 for fastening to the torso attachment device 30. Furthermore, the first and the second plain bearing 8a, 8b of the bracket 9 serve to receive and guide the lifting rod 7 at the bracket 9. The screws and rivets are not illustrated in the figures.

Figure 2:
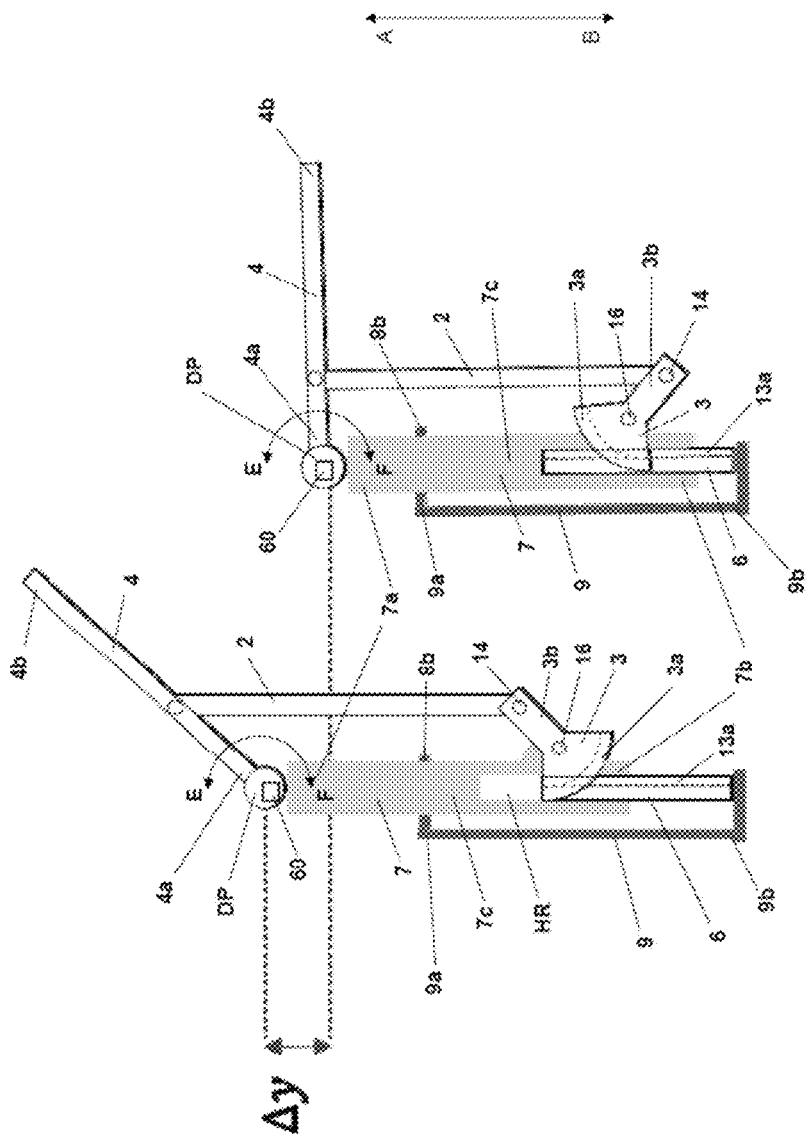
FIG. 2 shows a schematic side view of constituents of the exoskeleton according to the invention for supporting an arm of a user in a first and a second position.

In FIG. 2, only the first plain bearing 8a is shown.

Figure 4:
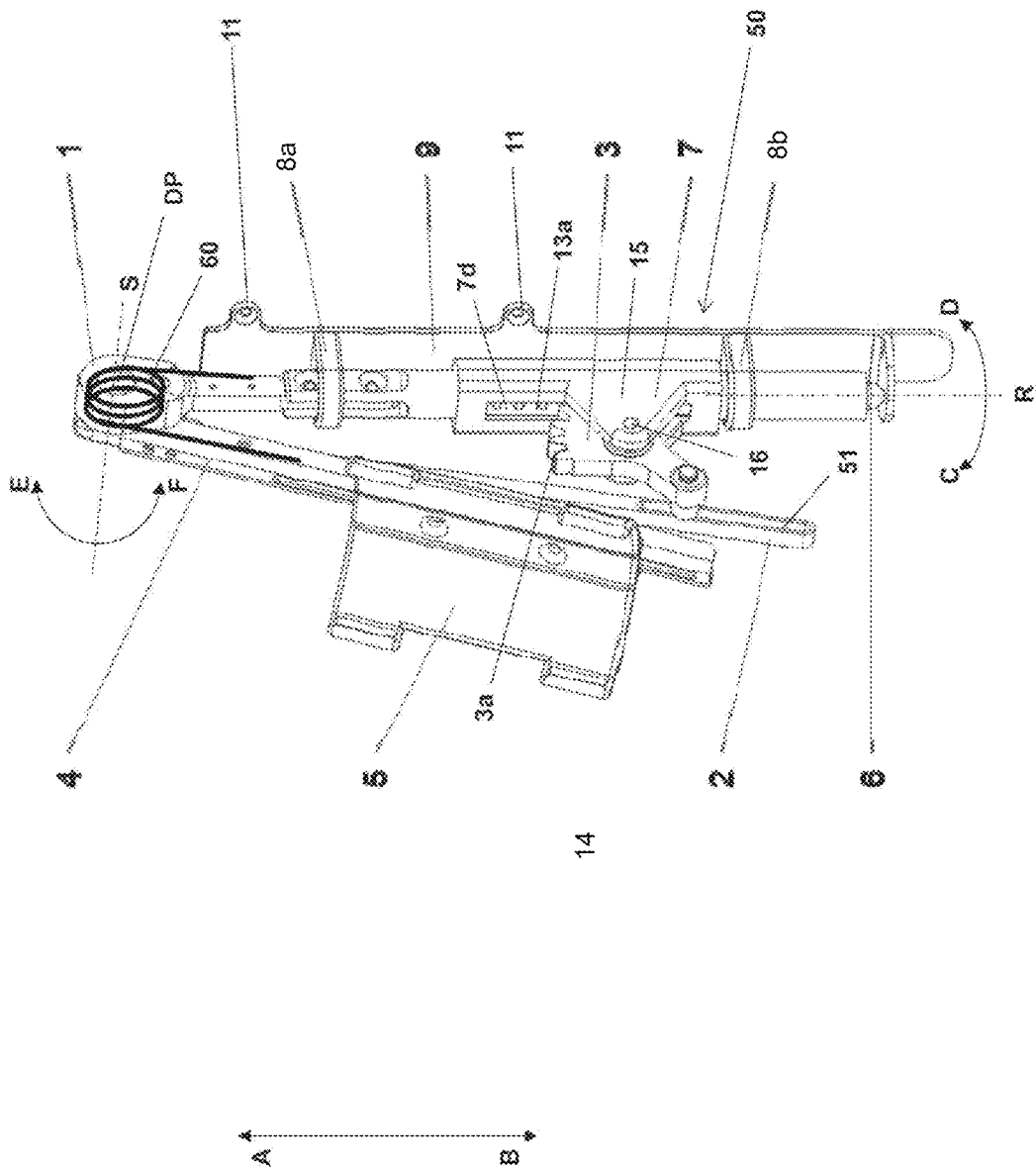
FIG. 4 shows a perspective view of a cantilever, a bracket, a spring element and a lifting rod of the exoskeleton according to the invention in the first setting.

Each of the plain bearings 8a, 8b contains a circular opening. In this case, the first plain bearing 8a is positioned in the vicinity of a first end 9a of the bracket 9 and the second plain bearing 8b is positioned in the vicinity of a second end 9b of the bracket 9 such that the lifting rod 7 is guided through the respective circular openings of the plain bearings 8a, 8b and as a result is connected to the bracket 9 in a movable manner and in a reversible manner in the arrow directions A and B. Furthermore, the bracket 9 contains a support plate 12 at the second end 9b. As shown in FIG. 4, the lifting rod 7 is mounted in a rotatable manner on the support plate 12 when the lifting rod 7 is positioned on the bracket 9. Alternatively, the support plate 12 can also have a concave or curved shape directed toward the lifting rod 7.

According to an advantageous embodiment, the lifting rod 7, as shown in FIGS. 4 to 8, is configured substantially as a tube with a first end 7a and a second end 7b. This configuration of the lifting rod 7 can also be referred to as a pipe or sleeve. As is apparent in particular from FIG. 4, the first end 7a of the lifting rod 7 extends beyond the first end 9a of the bracket 9 in the arrow direction A. It is apparent from FIG. 2 that the lifting rod 7 configured as a tube contains a cavity HR, which extends from the second end 7b approximately as far as the middle 7c of the lifting rod 7. The cavity HR can also be referred to as a blind hole or cutout.

According to an advantageous embodiment, a support element 6 can be introduced into the cavity HR of the lifting rod 7. The support element 6 can be configured in a cylindrical manner and be adapted in its shape to the cavity HR of the lifting rod 7. The lifting rod 7 and the support element 6 are reversibly movable with respect to one another in the arrow directions A and B. The support element 6 serves substantially to support the lifting rod 7 and to increase stability when the lifting rod 7 is moved relative to the bracket 9. As will be described below, the support element 6 can also be configured with teeth and thus in the form of a rack.

As already mentioned above, the lifting rod 7 is connected to the bracket 9 such that the lifting rod 7 extends through the openings of the first and second plain bearings 8a, 8b. As a result, the lifting rod 7 is movable relative to the bracket 9 in a reversible manner in a first arrow direction A and a second arrow direction B. In other words: the lifting rod 7 can be moved in the arrow direction A and in the arrow direction B relative to the bracket 9. Moreover, the lifting rod 7 can be rotated about the axis of rotation R in the direction of rotation C or D relative to the bracket 9 by means of the first and second plain bearings 8a, 8b.

The cantilever 4 is configured substantially as a rod with a first end 4a and a second end 4b. The rod can also be referred to as an arm, support, bar or lever. As illustrated in FIGS. 4 to 9, an armrest 5 is positioned on the cantilever 4. The armrest 5 serves to receive and hold an upper arm of a user AW. In order to temporarily fix the arm to the armrest 5, an arm strap having a closure is provided. The arm strap and the closure are illustrated in FIG. 3. The closure is in this case configured for example as a touch-and-close fastener.

As shown in FIGS. 2 to 9, the spring element 60 is configured as a leg spring with a first leg 60a and a second leg 60b. The spring element 60 is in this case positioned between the cantilever 4 and the lifting rod 7 such that the first leg 60a bears against the lifting rod 7 and the second leg 60b bears against the cantilever 4. The spring force of the spring element 60 configured as a leg spring thus has the effect that the cantilever 4 and the lifting rod 7 are pushed away from one another in the direction of rotation E. As indicated in the figures, the spring element 60 is positioned around the joint element 1.

Since the spring force of the spring element 60 continuously urges the cantilever 4 in the direction of rotation E and thus away from the lifting rod 7, the spring element 60 supports or pushes an arm of a user AW which is connected to the cantilever 4 via the armrest 5, in the direction of rotation E. As a result, the arms are supported and a load, for example a power tool held in the arms, is pushed upward in the arrow direction A. As a result, the load appears to be lighter and the user AW can hold the load for longer. As a result, the weight force of the load (for example power tool) is dissipated via the arms to the cantilever 4, the lifting rod 7, the bracket 9 and finally to the torso attachment device 30. The power tool is not illustrated in the figures.

According to a further advantageous configuration, the exoskeleton 10 furthermore contains a coupling rod 2, which is configured substantially as a bar with a first end and a second end (cf. FIGS. 4 to 9). The coupling rod 2 is connected to the cantilever 4 in a rotatable manner by the first end and connected to the lifting rod 7 again in a rotatable manner by the second end via a compensating mechanism 50. The coupling rod 2 serves substantially as a support and guide when the cantilever 4 moves relative to the lifting rod 7.

According to an advantageous embodiment (not shown in the figures) of the exoskeleton 10 according to the invention, the compensating mechanism 50 can be configured in the form of a slot 51 at the second end of the coupling rod 2 and of a pivot bearing on the lifting rod 7. The pivot bearing is in this case positioned in the slot 51 and movable along the slot 51 and in a manner guided by the slot 51. With the aid of the compensating mechanism 50 configured as a slot and pivot bearing, a movement of the coupling rod 2, when the cantilever 4 is rotated relative to the lifting rod 7, can be compensated.

According to a further embodiment, shown in FIGS. 4 to 9, of the exoskeleton 10 according to the invention, the compensating mechanism 50 can be configured in the form of a slot 51 at the second end of the coupling rod 2, of a sector gear 3, of a rack 13, and of a pivot bearing 14.

The optional support element 6 is configured in the form of the rack 13 according to the embodiment, shown in FIGS. 4 to 9, of the exoskeleton 10 according to the invention. According to an advantageous embodiment of the exoskeleton 10 according to the invention, it is also possible for both a support element 6 and a rack 13 to be positioned alongside one another on the support plate 12.

The cylindrically configured rack 13 projects into the interior of the lifting rod 7 such that the longitudinal extent of the rack 13 and the longitudinal extent of the lifting rod 7 are oriented parallel to one another.

As is apparent in particular from FIG. 4, the lifting rod 7 has a cutout 7d, which provides access to the teeth of the rack 13. The rack 13 is connected to the second end 7b of the lifting rod 7 and in particular to the support plate 12 at the second end 7b of the lifting rod 7 so as to be rotatable about the axis of rotation R in the direction of rotation C or D by means of a pivot bearing (not shown). In this case, the rack 13 is connected to the support plate 12 such that the rack 13 cannot be moved in the arrow direction A or B bracket. As a result, there is no relative movement between the rack 13 and the bracket 9.

On account of the possibility of the rack 13 and the lifting rod 7 being able to move relative to one another in the arrow direction A or B and because the rack 13 is introduced into the interior of the lifting rod 7, the combination or the cooperation of the rack 13 and the lifting rod 7 can be referred to as a piston-cylinder unit. In this case, the rack 13 is implemented as a piston and the lifting rod 7 and in particular the cavity HR of the lifting rod 7, is implemented as a cylinder for receiving the piston configured as a rack.

Furthermore, the lifting rod 7 contains a holding device 15 having a pivot pin 16, which serves to receive and hold the sector gear 3. By way of the holding device 15 having the pivot pin 16, the sector gear 3 can be rotated relative to the lifting rod 7 such that the teeth 3a of the sector gear 3 can mesh with the teeth 13 of the rack 13. The sector gear 3 furthermore contains a lever element 3b, at the free end of which the pivot bearing 14 is positioned. The pivot bearing 14 is positioned in the slot 51 and freely movable along the slot 51 and guided along the slot 51.

The cantilever 4 can, as a result of its rotary mounting at the pivot point DP with respect to the bracket 9, be brought reversibly into a first, second or third position.

Figure 5:
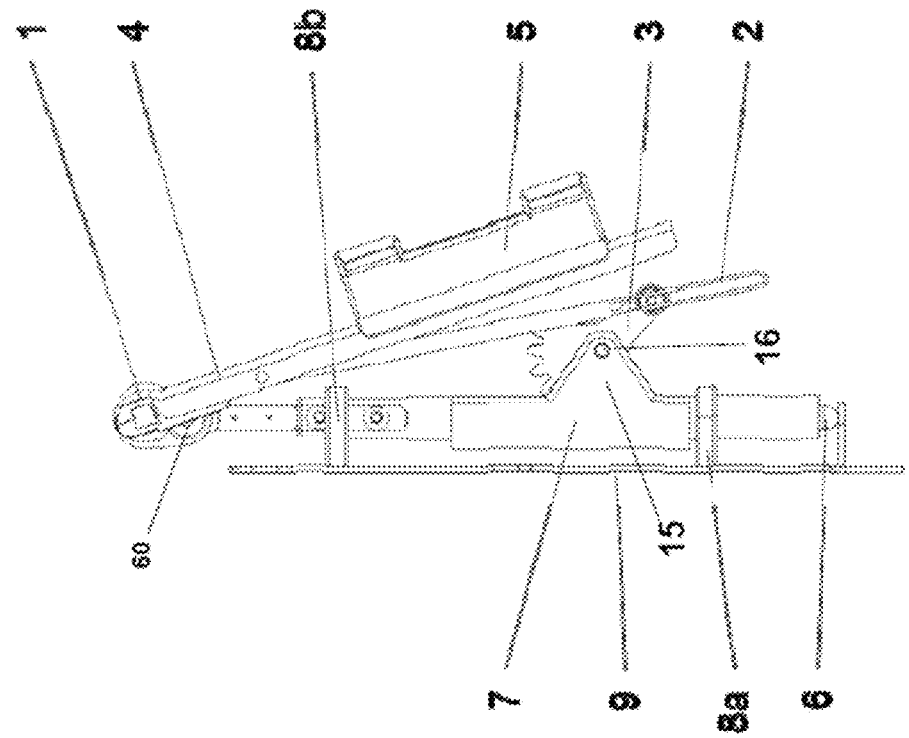
FIG. 5 shows a side view of the cantilever, the bracket, the spring element and the lifting rod of the exoskeleton according to the invention in the first setting.

FIGS. 4 and 5 show the exoskeleton 10 with the cantilever 4 in the first position.

Figure 6:
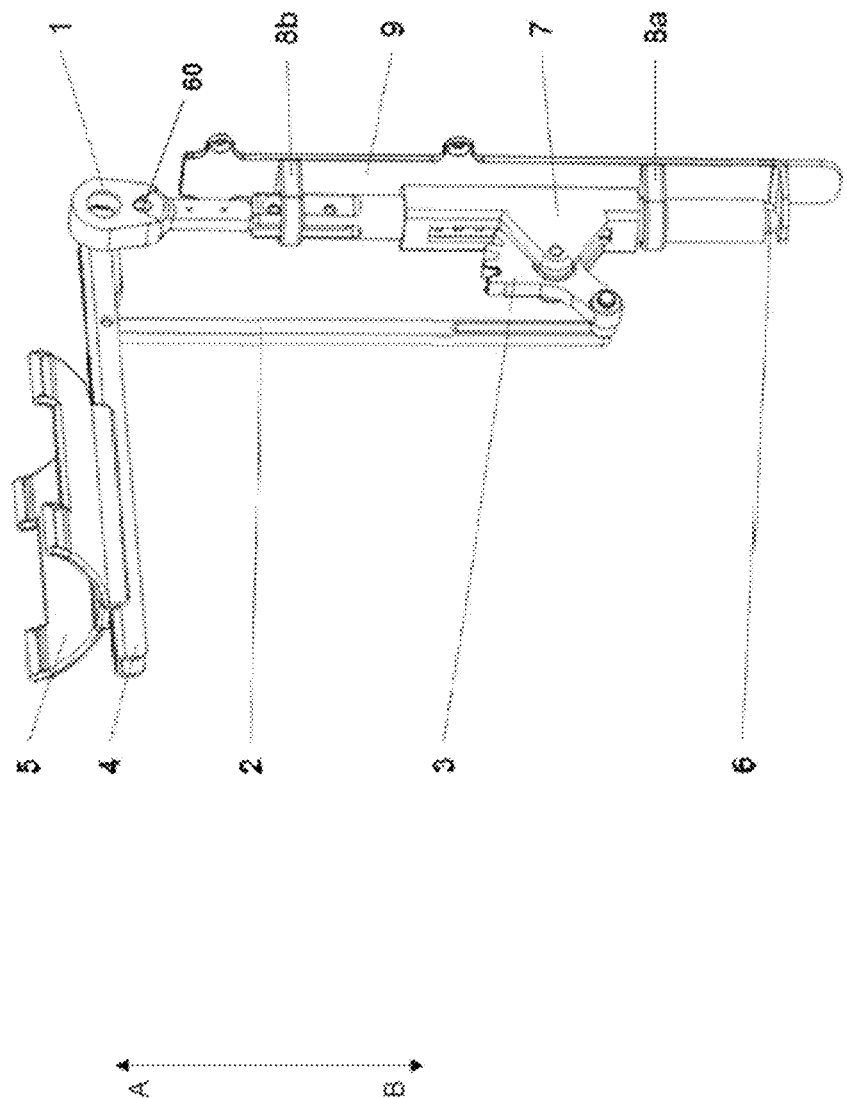
FIG. 6 shows a perspective view of the cantilever, the bracket, the spring element and the lifting rod of the exoskeleton according to the invention in the second setting.

FIGS. 6 and 7 show the cantilever 4 in the second position.

Figure 9:
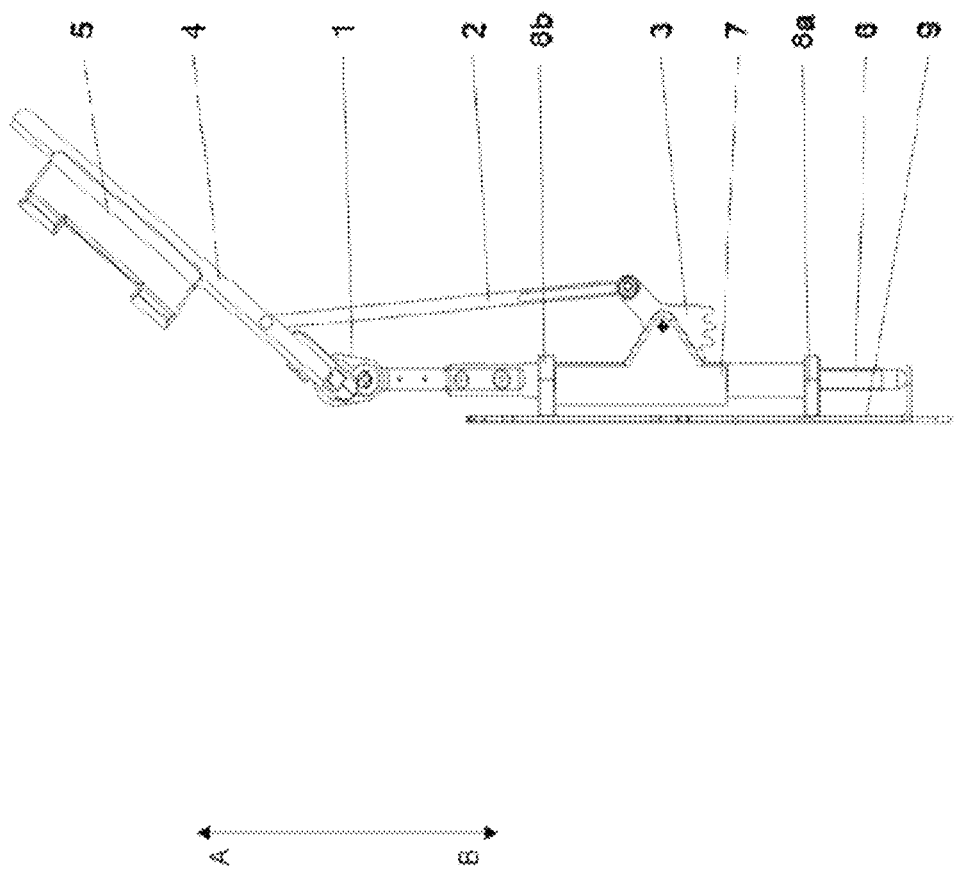
FIG. 9 shows a side view of the cantilever, the bracket, the spring element and the lifting rod of the exoskeleton according to the invention in the third setting.

FIGS. 8 and 9 illustrate the cantilever 4 in the third position.

In the first position, the second end 4b of the cantilever 4 is inclined downward in the arrow direction B.

In the second position, the second end 4b of the cantilever 4 is substantially horizontal.

In the third position, the first end 4a of the cantilever 4 points upward in the arrow direction A.

When the user AW moves the arm that is connected to the cantilever 4 upward in the arrow direction A, the lifting rod 7 is likewise pulled upward in the arrow direction A via the joint element 1. Since the lifting rod 7 is mounted so as to be movable in the arrow direction A or B with respect to the bracket 9, the pivot point DP can compensate the travel Δy for compensating the anatomical movement of the human shoulder 40 during the lifting of an arm. Such compensation adapts the exoskeleton better to the actual anatomy and the actual sequence of movements of the human user AW while lifting loads, and increases the wearing comfort of the exoskeleton.

LIST OF REFERENCE CHARACTERS

1: Joint element
2: Coupling rod
3: Sector gear
3a: Teeth of the sector gear
3b: Lever element
4: Cantilever
4a: First end of the cantilever
4b: Second end of the cantilever
5: Armrest
6: Support element
7: Lifting rod
7a: First end of the lifting rod
7b: Second end of the lifting rod
7c: Middle of the lifting rod
7d: Cutout in the lifting rod
8a: First plain bearing
8b: Second plain bearing
9: Bracket
9a: First end of the bracket
9b: Second end of the bracket
10: Exoskeleton 11: Cutouts in the bracket
12: Support plate
13: Rack
13a: Teeth of the rack
14: Pivot bearing
15: Holding device
16: Pivot pin of the holding device
20: Arm of the user
30: Torso attachment device
40: Shoulders of the user
50: Compensating mechanism
51: Slot
60: Spring element
60a: First leg of the spring element
60b: Second leg of the spring element
HR: Cavity of the lifting rod
DP: Pivot point
OK: Upper body
AW: User
VS: Closure
R: Axis of rotation of the lifting rod
C, D: Directions of rotation of the lifting rod
S: Axis of rotation of the cantilever
E, F: Directions of rotation of the cantilever

The invention claimed is:

1. An exoskeleton for supporting an arm of a user, comprising:
 a torso attachment device releasably connecting the exoskeleton to a torso of the user;
 a bracket connected to the torso attachment device;
 a lifting rod connected to the torso attachment device via the bracket and which is reversibly movable in a first direction and a second direction relative to the bracket;
 a cantilever configured to support an upper arm of the user, wherein the cantilever is releasably connectable to the upper arm of the user; and
 a spring element configured to exert a force on the cantilever and the lifting rod so as to assist in supporting a load lifted overhead by the user while the upper arm of the user is supported by the cantilever which simultaneously moves the lifting rod in the first direction.

2. The exoskeleton according to claim 1 further comprising a coupling rod having a first end and a second end, wherein the coupling rod is rotatably connected to the cantilever by the first end and to the lifting rod via a compensating mechanism by the second end.

3. The exoskeleton according to claim 2, wherein the compensating mechanism comprises a slot at the second end of the coupling rod and a pivot bearing on the lifting rod and wherein the pivot bearing is disposed in the slot.

4. The exoskeleton according to claim 2, wherein the compensating mechanism comprises a slotted guide disposed between the second end of the coupling rod and the lifting rod.

5. The exoskeleton according to claim 2, wherein the compensating mechanism comprises a sector gear and a rack and wherein the sector gear is rotatably connected to the lifting rod such that teeth of the sector gear mesh with teeth of the rack.

6. The exoskeleton according to claim 5, wherein the lifting rod and the rack are configured as a piston-cylinder unit.

* * * * *